United States Patent
Peter et al.

(10) Patent No.: US 9,562,810 B2
(45) Date of Patent: Feb. 7, 2017

(54) DEFORMABLE INTERFEROMETRIC SENSOR USING A POLYMER BETWEEN REFLECTORS TO MEASURE ANALYTE ABSORPTION

(71) Applicant: Yves-Alain Peter, Terrebonne (CA)

(72) Inventors: Yves-Alain Peter, Terrebonne (CA); Raphael St-Gelais, Montreal (CA)

(73) Assignee: POLYVALOR, LIMITED PARTNERSHIP, Montreal (CA)

( * ) Notice: Subject to any disclaimer, the term of this patent is extended or adjusted under 35 U.S.C. 154(b) by 59 days.

(21) Appl. No.: 14/649,985

(22) PCT Filed: Dec. 9, 2013

(86) PCT No.: PCT/CA2013/001021
§ 371 (c)(1),
(2) Date: Jun. 5, 2015

(87) PCT Pub. No.: WO2014/085916
PCT Pub. Date: Jun. 12, 2014

(65) Prior Publication Data
US 2015/0292880 A1     Oct. 15, 2015

Related U.S. Application Data

(60) Provisional application No. 61/734,634, filed on Dec. 7, 2012.

(51) Int. Cl.
*G01J 3/26* (2006.01)
*G01N 21/45* (2006.01)
*G01N 21/77* (2006.01)

(52) U.S. Cl.
CPC ............ *G01J 3/26* (2013.01); *G01N 21/45* (2013.01); *G01N 2021/7723* (2013.01); *G01N 2021/7779* (2013.01)

(58) Field of Classification Search
CPC ... G01B 11/161; G01B 2290/25; G02B 26/00; G01J 3/26; G01J 3/0218; G01N 21/17; G01N 21/75; G01N 2021/7779; G01N 2021/7723
See application file for complete search history.

(56) References Cited

U.S. PATENT DOCUMENTS

| | | | |
|---|---|---|---|
| 7,776,611 B2 | 8/2010 | Crudden et al. | |
| 8,174,698 B2 | 5/2012 | Peter et al. | |
| 2006/0227330 A1* | 10/2006 | Hjelme | G01N 21/45 356/481 |

(Continued)

OTHER PUBLICATIONS

Gauglitz et al., "Chemical and biochemical sensors based on interferometry at thin (multi-)layers", Sensors and Actuators B, 11 (1993) 21-27.

(Continued)

*Primary Examiner* — Michael P Lapage
(74) *Attorney, Agent, or Firm* — Norton Rose Fulbright Canada LLP

(57) ABSTRACT

There is described a deformable interferometric sensor in which polymer swelling, upon analyte absorption, is used to deform an on-chip silicon Fabry-Perot interferometer (FPI). The magnitude of the deformation, recorded through the resonance wavelength shift, is proportional to the analyte concentration.

16 Claims, 8 Drawing Sheets

(56) References Cited

U.S. PATENT DOCUMENTS

| | | | | |
|---|---|---|---|---|
| 2006/0227331 A1* | 10/2006 | Vollmer | ................ | G01N 21/23 |
| | | | | 356/483 |
| 2009/0257113 A1* | 10/2009 | Smith | ................. | G02B 26/001 |
| | | | | 359/321 |
| 2010/0238454 A1* | 9/2010 | Pruessner | ............. | G01G 3/165 |
| | | | | 356/479 |
| 2012/0189025 A1* | 7/2012 | Zheng | ................... | H01S 5/1071 |
| | | | | 372/20 |
| 2013/0169970 A1* | 7/2013 | Fan | .......................... | G01J 3/45 |
| | | | | 356/454 |

OTHER PUBLICATIONS

St-Gelais et al., "A Fabry-Perot refractometer for chemical vapor sensing by solid-phase microextraction", Department of Engineering Physics, Ecole Polytechnique de Montreal, Quebec, Canada, Department of Chemistry, Queen's University, Kingston, Ontario, Canada, 2011.

Martinez-Hipatl et al., "Detection of volatile organic compounds by an interferometric sensor", Sensors and Actuators B: chemical, 2010, 37-42.

Reddy et al., "Rapid, sensitive, and multiplexed on-chip optical sensors for micro-gas chromatography", Lab on a Chip, The Royal Society of Chemistry 2012, 12, 901.

Aussenegg et al., "The metal island coated swelling polymer over mirror system (MICSPOMS): a new principle for measuring ionic strength", Sensors and Actuators B 29 (1995), 204-209.

* cited by examiner

DEFORMABLE INTERFEROMETRIC SENSOR USING A POLYMER BETWEEN REFLECTORS TO MEASURE ANALYTE ABSORPTION

CROSS-REFERENCE TO RELATED APPLICATIONS

The present patent application is a US National Stage of International Application No. PCT/CA2013/001021, filed on Dec. 9, 2013, which claims priority of US provisional Application Ser. No. 61/734,634, filed on Dec. 7, 2012.

TECHNICAL FIELD

The present invention relates to the field of chemical sensors, and more particularly to chemical sensors that use polymer swelling upon analyte absorption.

BACKGROUND OF THE ART

Polymer swelling is a phenomenon that occurs when certain polymers absorb analytes, whereby expansion of the polymer can be used to create chemical sensors for artificial olfaction systems. Such systems are intelligent chemical instruments for the detection of volatile compounds and smells. Certain applications, such as gas chromatography, require high limits of detection (LOD) in order to detect volatile organic compounds. The LOD is usually defined as the analyte concentration that produces a response corresponding to three (3) times the standard deviation (std) of the background noise signal.

While there exists several micromechanical sensor technologies for chemical sensing, such as cantilever, Surface Acoustic Wave (SAW), and Quartz Crystal Microbalance (QCM), there is a need to develop new devices that are better suited for applications that require a large dynamic range, field deployment, and passive remote interrogation.

SUMMARY

There is described a deformable interferometric sensor in which polymer swelling, upon analyte absorption, is used to deform an on-chip silicon Fabry-Perot interferometer (FPI). The magnitude of the deformation, recorded through the resonance wavelength shift, is proportional to the analyte concentration.

The chemical sensor is based on in-plane silicon Fabry-Perot interferometers functionalized with polymers. Upon analyte absorption, polymer swelling and refractive index variations induce strong shifts of the interferometer resonance wavelengths. Mechanical deformations are thus the dominant sensing mechanism, in accordance with analytical and finite element models.

The deformable in-plane FPI sensors may be used for field deployment and remote interrogation as there is no need for any local source of energy to operate. Sensor heads may be deployed in industrial workplaces or for environmental monitoring, and may be linked to an interrogation system through passively aligned single mode optical fibers. Using a 1×N optical switch may also allow the readout of multiple sensors (for various locations and/or for various polymers) using a single laser and photodetector.

The deformable in-plane sensors are integrable. The in-plane configuration allows monolithic integration of microfluidic systems, which simplifies parallel functionalization of multiple interferometers with different polymers. Integrated fiber alignment grooves also allow passive alignment of optical fibers (e.g. input and output optical fibers), facilitating remote interrogation by avoiding the need for on-site free-space alignment. Finally, successful interfacing of swellable polymers with a silicon optical microsystem allows flexibility in the design of other interferometric, micromechanical, or even electromechanical systems that may be used to maximize sensitivity to polymer swelling.

In accordance with a first broad aspect, there is provided a deformable interferometric sensor comprising: a pair of parallel and spaced apart reflectors forming a Fabry-Perot cavity, each one of the reflectors having an outer surface and an inner surface, the pair of reflectors separated by a distance L; an optical fiber interfaced with the outer surface of each one of the reflectors and having an optical axis that intersects the pair of reflectors; and a polymer provided between the reflectors, the polymer exhibiting expansion along the optical axis of the optical fiber upon absorption of at least one analyte, and inducing a shift of a resonance wavelength substantially proportional to a concentration of the at least one analyte as absorbed, the expansion causing an increase in the distance L between the reflectors and deforming the Fabry-Perot cavity.

In some embodiments, the polymer has opposite sides and is provided between the reflectors with each one of the opposite sides adjacent a corresponding one of the reflectors, the polymer embedded in the optical fiber such that the expansion of the polymer at the opposite sides is constrained by the optical fiber and by the corresponding one of the reflectors.

In some embodiments, at least one of the reflectors is fixed and has a spring constant $K_{reflector}$ and the polymer has a spring constant $K_{poly}$ greater than the spring constant $K_{reflector}$ such that the expansion of the polymer occurs in an in-plane direction and causes a deformation of the at least one of the reflectors, thereby increasing the distance L between the reflectors and deforming the Fabry-Perot cavity.

In some embodiments, the spring constant $K_{poly}$ is given by:

$$K_{poly} = \frac{whE_{poly}}{L},$$

and the spring constant $K_{reflector}$ follows:

$$K_{reflector} < \frac{whE_{poly}}{L},$$

where $E_{poly}$ is a Young's modulus of the polymer, w a width of each one of the reflectors, and h a height of each one of the reflectors.

In some embodiments, a condition for the deformation of the at least one of the reflectors is given by:

$$\frac{t^3}{w^4} < \frac{E_{Poly}}{32E_{Si}L},$$

where the at least one of the reflectors comprises a silicon layer having a Young's modulus $E_{si}$ and each one of the reflectors has a thickness t.

In some embodiments, at least one of the reflectors is displaceable by means of a displacement mechanism connected thereto, the displacement mechanism comprising a biasing member having a spring constant $K_{bias}$ lower than a spring constant $K_{poly}$ of the polymer such that the expansion of the polymer causes a change in deflection of the biasing member and the displacement of the at least one of the reflectors, thereby increasing the distance L between the reflectors and deforming the Fabry-Perot cavity.

In some embodiments, at least one of the deformation of the Fabry-Perot cavity and the increase in the distance L between the reflectors, a first variation in a refractive index of the polymer resulting from mixture of the polymer with the at least one analyte upon the absorption thereof, the at least one analyte having a refractive index different than the refractive index of the polymer, and a second variation in the refractive index of the polymer resulting from a hydrostatic stress experienced by the polymer upon the expansion thereof, the hydrostatic stress created by the reflectors opposing at least one force to the expansion causes the polymer to induce the shift of the resonance wavelength.

In some embodiments, the reflectors are Bragg mirrors each comprising at least two layers of silicon formed in a substrate of optical material by vertical plasma etching.

In some embodiments, the reflectors comprise a reflective metallic layer, a multilayer assembly of materials exhibiting refractive index contrast, or a combination thereof.

In some embodiments, the optical fiber is one of a single mode fiber and a multi-mode fiber.

In some embodiments, the polymer comprises a polymer composite having one of a carbon-rich and a silicon-rich backbone.

In some embodiments, the sensor further comprises a first and a second elongate groove configured to respectively receive therein a first one and a second one of the optical fiber and to align the first and second ones of the optical fiber.

In accordance with another broad aspect, there is provided a method for determining a concentration of an analyte, the method comprising: providing a polymer inside a Fabry-Perot cavity formed by a pair of parallel and spaced apart reflectors, the polymer exhibiting expansion and causing deformation of the cavity upon absorption of the analyte, the polymer having a spring constant $K_{poly}$ greater than a spring constant of at least one of the reflectors $K_{reflector}$; measuring a shift of a resonance wavelength induced by expansion of the polymer; and converting the shift of the resonance wavelength into the concentration of the analyte.

In some embodiments, providing the polymer inside the Fabry-Perot cavity comprises providing a microfluidic channel in a space between the reflectors, providing a reservoir in fluid communication with the microfluidic channel, placing the polymer in the reservoir, the polymer flowing by a capillary force from the reservoir into the microfluidic channel to fill the space between the reflectors, and curing the polymer at room temperature for a predetermined time period.

In some embodiments, providing the polymer comprises providing the polymer where the spring constant $K_{poly}$ is given by:

$$K_{poly} = \frac{whE_{poly}}{L},$$

and the spring constant $K_{reflector}$ follows:

$$K_{reflector} < \frac{whE_{poly}}{L},$$

where $E_{poly}$ is a Young's modulus of the polymer, w a width of each one of the reflectors, h a height of each one of the reflectors, and L is a distance between the reflectors.

In some embodiments, providing the polymer comprises providing the polymer where a condition for a deformation of at least one of the reflectors is given by $$\frac{t^3}{w^4} < \frac{E_{Poly}}{32E_{Si}L},$$

where the at least one of the reflectors comprises a silicon layer having a Young's modulus $E_{si}$ and each one of the reflectors has a thickness t.

In some embodiments, providing the polymer comprises providing a polymer composite having one of a carbon-rich and a silicon-rich backbone.

In some embodiments, measuring the shift of the resonance wavelength induced by expansion of the polymer comprises scanning a tunable laser source interfaced with the Fabry-Perot cavity through an optical fiber, the optical fiber interfaced with an outer surface of each one of the reflectors, recording using a photodetector at least one transmission spectrum of the Fabry-Perot cavity at predetermined time intervals, determining a position of the resonance wavelength of the recorded at least one transmission spectrum, and comparing the determined position of the resonance wavelength to an initial position of the resonance wavelength for obtaining the shift.

In some embodiments, the method further comprises applying a filter to the recorded at least one transmission spectrum, thereby obtaining a plurality of filtered resonance peaks, and determining the position of the resonance wavelength comprises fitting a fourth order polynomial to a top half of the filtered resonance peaks.

BRIEF DESCRIPTION OF THE DRAWINGS

Further features and advantages of the present invention will become apparent from the following detailed description, taken in combination with the appended drawings, in which:

FIG. 5b illustrates a higher magnification view of the Fabry-Perot interferometer and the optical fiber alignment grooves from FIG. 5a;

It will be noted that throughout the appended drawings, like features are identified by like reference numerals.

DETAILED DESCRIPTION

Figure 1:
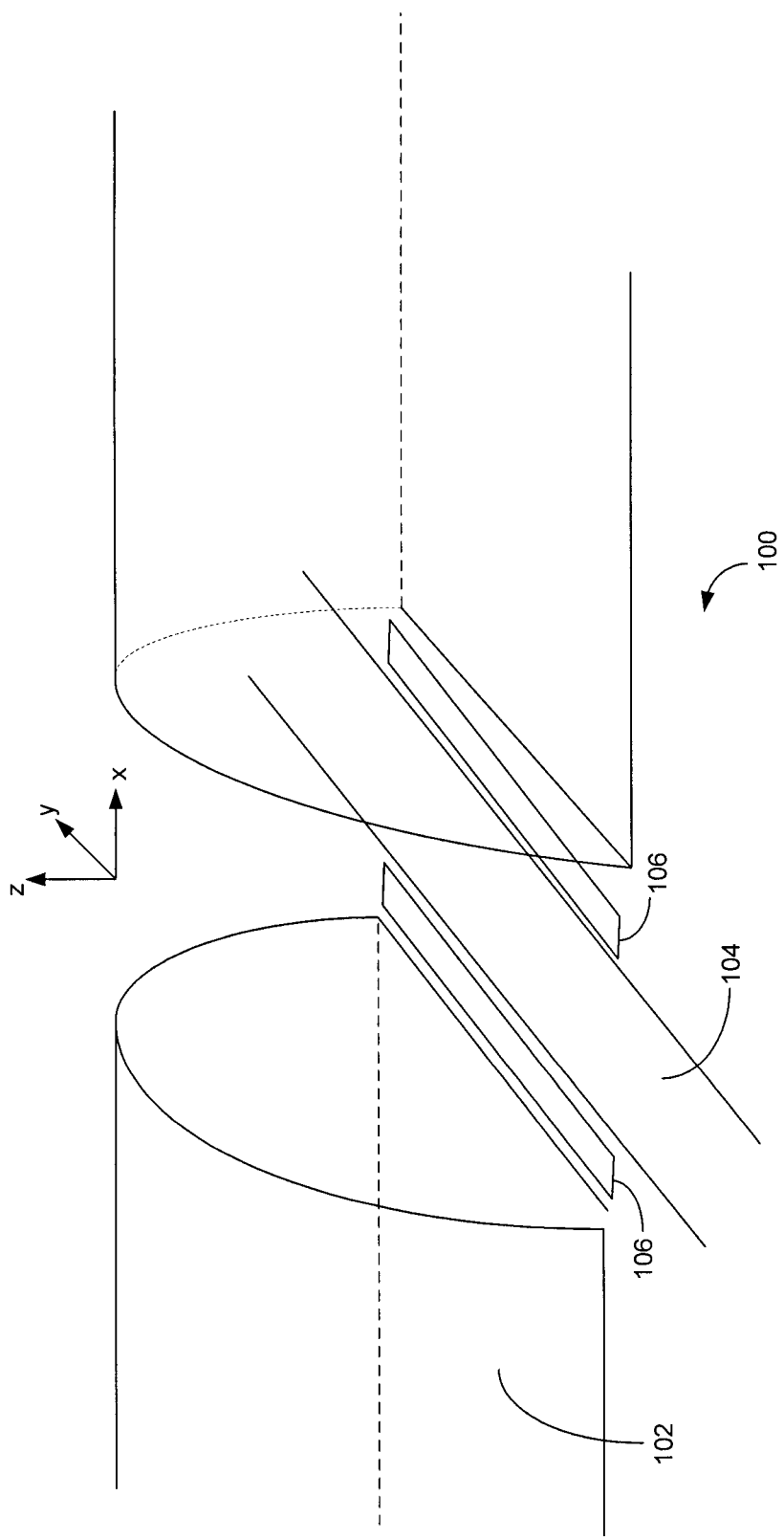
FIG. 1 is schematic representation of an exemplary deformable interferometric sensor.

Referring to FIG. 1, there is illustrated an exemplary deformable interferometric sensor 100. Upon sample absorption, polymer expansion deforms the interferometer, inducing a shift of its resonance wavelength. As illustrated, an optical fiber 102 is embedded with an absorbent polymer 104 surrounded by a pair of reflectors 106, thus forming a Fabry-Perot cavity. This configuration will be referred to herein as "in-plane" as the polymer swelling occurs in an in-plane direction. In some embodiments, the reflectors 106 are both fixed and sufficiently flexible such that polymer expansion causes deformation of the cavity via deformation of the reflectors. Alternatively, one or both reflectors 106 may be displaceable via a mechanism connected to the reflector(s) 106 such that the cavity is deformed via reflector displacement (instead of reflector deformation). The displacement mechanism may be used to control displacement of the reflector(s) 106 so as to cause a shift in resonance wavelength substantially proportional to the concentration of absorbed analyte. In one embodiment, at least one of the reflectors 106 is rigid and the displacement mechanism comprises a biasing member, such as one or more springs, formed in the substrate in which the reflectors 106 are formed. The biasing mechanism illustratively supports the rigid reflector(s) 106 and, upon being deflected under a load, causes displacement of the reflector(s) 106. In some embodiments, a combination of reflector displacement and reflector deformation is used to deform the cavity. The present description thus refers generally to cavity deformation and increased reflector separation.

The polymeric composite 104 may be any of numerous polymers, whose backbone is Carbon- or Silicon-rich. These polymeric composites behave as absorbents for volatile compounds and undergo reversible chemical interactions: dipole-dipole interactions, charge-transfer or coordination complexes, for example. The composite may be composed of one single polymer, a cross-linked polymer, a block-copolymer, a polymer modified with a particular side-chain functionality specific to a certain volatile compound, a polymer mixed with small absorbent molecules or a mixture of the aforementioned polymers such that gas absorption is improved. Suitable polymers with Carbon-rich backbones have a structure that is composed in majority or in-part, of polymers such as Polyvinylchloride, Polyepichlorohydrin, polyethylene oxide, polypyrrole, polystyrene, polyacrylic acid, polybutadiene, polypropylene, polymethylmethacrylate or polylactic acid. Suitable Silicon-rich backbones polymers have a structure that is linear, branched or cross-linked and is siloxane based. Examples are Polydimethylsiloxane, Polydiphenylsiloxane or AminoethylaminopropylMethylsiloxane. Other polymers that are formed by hydrosilylation of vinyl and/or hydride containing siloxane polymers with bi-functional silanes having vinyl and/or hydride functionalities may also be used.

The reflectors 106 may be Bragg mirrors of two, three, or more layers of silicon deposited on a substrate (not shown) of glass or some other optical material. More particularly, the reflectors 106 may be silicon-air Bragg mirrors formed in a substrate by vertical plasma etching. Alternatively, the reflectors may also be any multilayer assembly of materials exhibiting refractive index contrast, any reflective metallic layer, or a combination of both. The optical fiber 102 may be a single mode fiber or a multi-mode fiber.

The configuration as illustrated in FIG. 1 differs from traditional configurations for Fabry-Perot sensors, where the polymer 104 is not embedded in the fiber 102 but is instead provided separate therefrom. When separate from the fiber 102, the polymer 104 is bonded to a rigid substrate such that swelling can only occur in an out-of-plane direction, which is parallel to the optical axis. There is also no force opposing the movement of the top material interface that is used as the movable mirror of the interferometer. In contrast, when embedded in the fiber 102, both sides of the polymer 104 are constrained by the fiber 102 and by the mirror 106 on each side of the polymer 104 and thus special considerations are needed.

Figure 2:
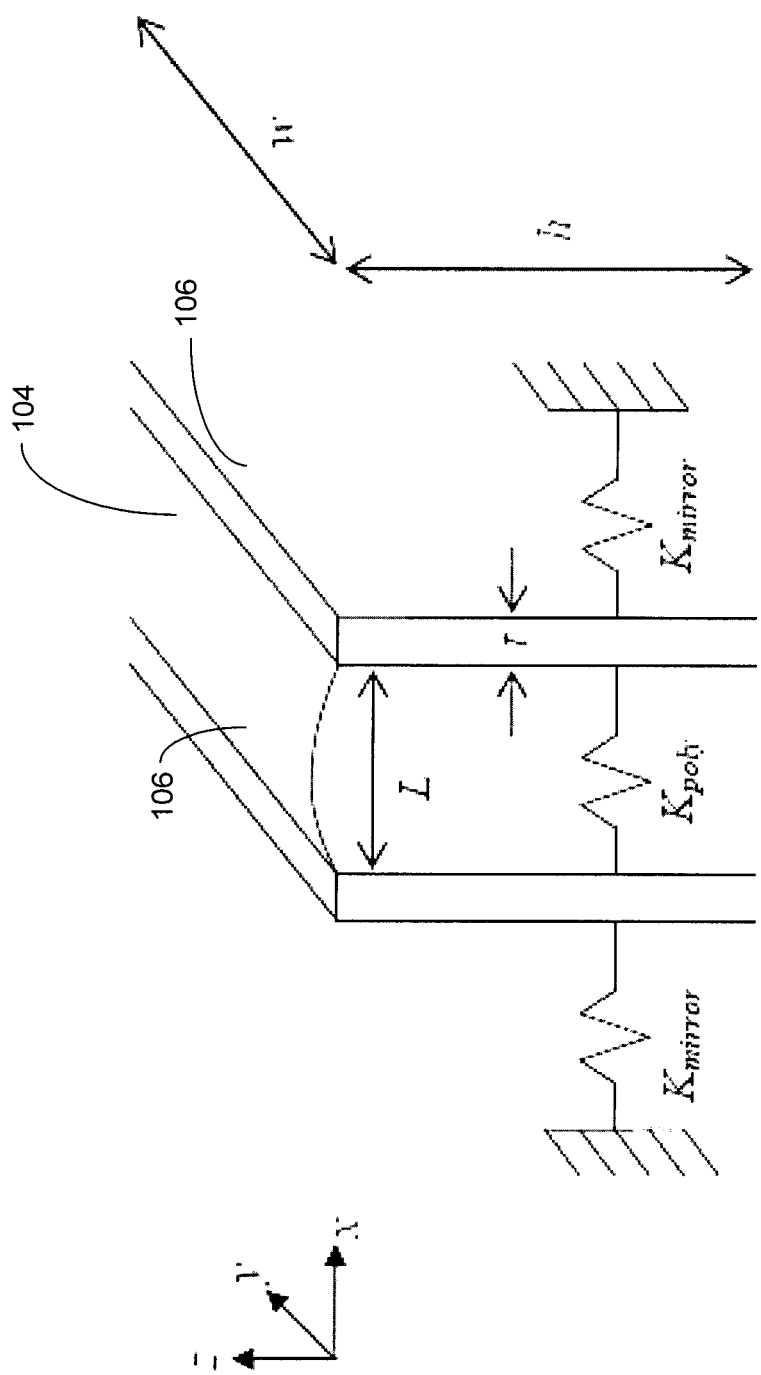
FIG. 2 is a schematic representation of the polymer and mirrors from the sensor of FIG. 1 with arbitrary dimensions.

For the polymer 104 to be able to move a mirror 106 in the x direction (upon a ΔL polymer expansion due to the absorption of a given volume fraction of analyte) a spring constant of the polymer 104 ($K_{poly}$) must be higher than a spring constant of the mirrors 106 ($K_{mirror}$): $K_{mirror} < K_{poly}$. FIG. 2 schematically illustrates the polymer 104 and mirrors 106 with arbitrary dimensions. The spring constant of the polymer 104 may be given by:

$$K_{poly} = \frac{whE_{poly}}{L} \qquad (1)$$

where $E_{poly}$ is the Young's modulus of the polymer 104, h the height of the mirror layers, w the width of the mirror layers, and L the spacing between the mirrors 106. The following condition is consequently imposed to the spring constant of the mirrors 106:

$$K_{mirror} < \frac{whE_{poly}}{L} \qquad (2)$$

As discussed above, for an embodiment where one or more of the mirrors 106 are rigid and a displacement mechanism, such as a biasing member (e.g. a spring), is used to move the mirror(s) 106, the biasing member illustratively has a spring constant ($K_{bias}$) that respects the condition of equation (2), namely $K_{bias} < K_{poly}$, such that:

$$K_{bias} < \frac{whE_{poly}}{L}$$

In this manner, the expansion of the polymer illustratively causes a change in deflection of the biasing member and accordingly a displacement of the one or more mirrors 106. As a result, the distance L between the reflectors is increased and the Fabry-Perot cavity deformed.

For an embodiment where the mirror 106 consists of a silicon layer embedded at both extremities, a reduced spring constant is defined as the ratio of the spring constant over the width w of the layer: k=K/w, and the deformation condition is rewritten as: $k_{mirror} \ll k_{poly}$.

The reduced spring constant of the polymer 104 becomes:

$$k_{poly} = \frac{hE_{poly}}{L} \quad (3)$$

Using beam equations, the spring constant of the mirror layer, upon application of a uniformly distributed force over its surface, may be given by:

$$k_{beam} = \frac{32E_{Si}ht^3}{w^4} \quad (4)$$

The deformation condition may thus be rewritten as:

$$\frac{t^3}{w^4} < \frac{E_{poly}}{32E_{Si}L} \quad (5)$$

which indicates that very long (w) and thin (t) mirror layers are needed in order to obtain deformation, especially if the polymer is very soft ($E_{poly}$) compared with silicon ($E_{Si}$).

For example, the maximum possible thickness (t) of the silicon layer for a system having the following conditions was calculated:

L=35 µm $E_{poly}$=1.8 MPa $E_{Si}$=160 GPa w=130 µm

The result is that t<1.5 µm. Layers thicker than 1.5 µm would therefore not allow polymer expansion to deform the mirror layers and to produce a sensing response. In an exemplary embodiment where a third extremity of the system is embedded in the substrate, the condition stated above should still apply, as long as h>w/2.

Figure 3:
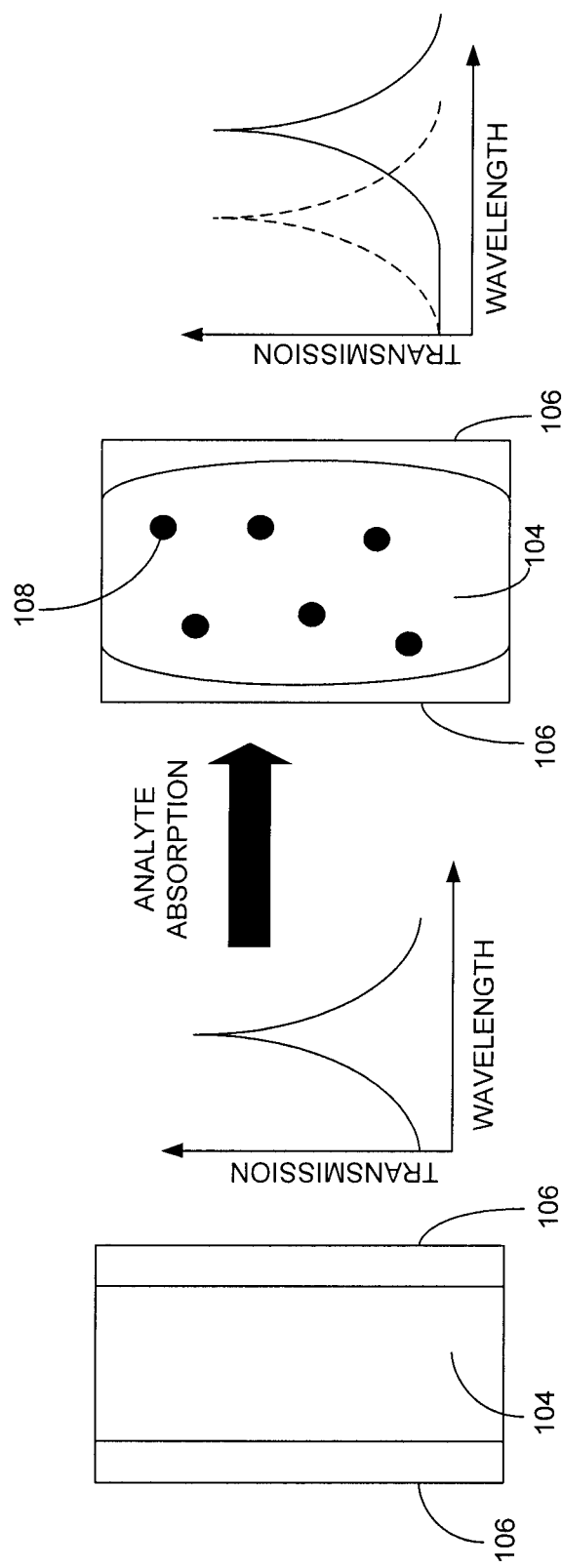
FIG. 3 is an exemplary illustration of the operating principle of the sensor of FIG. 1.

Referring now to FIG. 3, there is illustrated the principle of shifting ($\Delta\lambda_{Res}$) the interferometer resonance wavelength ($\lambda_{Res}$) upon analyte 108 absorption. Three factors may cause such shifts. First, polymer 104 swelling deforms the interferometer and increases ($\Delta L$) mirror 106 separation (L). Secondly, if the refractive index of the analyte 108 ($n_a$) and the polymer 104 ($n_p$) are different, the refractive index of the polymer-analyte mixture (n) should change by a factor $\Delta n_{Mix}$ upon sample absorption. Lastly, if the mirrors 106 oppose a significant force to the polymer 104 expansion, there should be a densification of the polymer 104, which should lead to a $\Delta n_\sigma$ variation of its refractive index. All three effects change the interferometer optical path length (nL), and contribute to the measured resonance wavelength shift ($\Delta\lambda_{Res}$) through:

$$\frac{\Delta\lambda_{Res}}{\lambda_{Res}} = \alpha\frac{\Delta L}{L} + \beta\frac{(\Delta n_{Mix} + \Delta n_\sigma)}{n} \quad (6)$$

where α=0.75 and β=0.93 are device-specific reduction factors (≤1). The factor α accounts for the fact that only one layer in each Bragg mirror 106 is displaced upon analyte 108 absorption. The factor β accounts for the fact that the resonant mode inside the cavity is not located entirely inside the polymer 104, but also partly inside the mirrors 106 (i.e., the thickness of the mirrors is not negligible compared to L, the distance between the mirrors 106).

The dimensionless sensitivity ($\Gamma_\phi$) may be defined as the normalized ratio of the resonance wavelength shift ($\Delta\lambda_{Res}$) to the absorbed volume fraction of analyte ($\phi_a$) inside the polymer:

$$\Gamma_\phi = \frac{1}{\lambda_{Res}}\frac{\Delta\lambda_{Res}}{\Delta\phi_a} \quad (7)$$

Conveniently, $\phi_a$ can be related to the volume/volume (v/v) concentration of analyte in air ($C_{air}$) near the polymer, using the ideal gas law and the partition coefficient of the polymer for the respective analyte ($K_{p-a}$):

$$\phi_a = K_{p-a}\frac{PV_m}{RT}C_{air} \quad (8)$$

where P is the pressure, T is the temperature, R is the gas constant and $V_m$ is the molar volume of the analyte, in liquid phase.

Note that for all the calculations presented herein, it is assumed that upon absorption, the final volume of the polymer-analyte mixture equals the initial volume of the polymer, plus the absorbed volume of analyte. In other words, it is assumed that there is no volume reduction upon absorption, except in the presence of mechanical stresses inside the polymer. These stresses lead to negligible volume reductions. In this context, the relative volume (V) expansion of the polymer upon absorption of a $\phi_a$ volume fraction of analyte is given by:

$$\frac{\Delta V}{V} = \Delta\phi_a \quad (9)$$

This assumption of volume additivity is supported by reports that the absorption of a slightly lower refractive index analyte (cyclohexane) reduces the refractive index of a PDMS-based polymer. This would not have been possible if significant volume reduction occurred upon absorption, since volume reduction would have led to an increase of the refractive index.

Sensitivity ($\Gamma_\phi$) of deformable Fabry-Perot Interferometer (FPI) sensors may be detailed in the case where: the mirrors are perfectly movable, such that they oppose negligible forces to the expansion of the polymer; and the volume increase of the polymer (i.e. swelling) is directed mainly in one direction, parallel to the optical pathlength between the mirrors (L), such that $\Delta L$ is maximized. Note that this is typically the case in an out-of-plane configuration but these conditions are non-trivial to meet for an in-plane configuration.

Under the two conditions listed above, it is possible to show that the relative length increase between the mirrors, upon absorption of a $\phi_a$ volume fraction of analyte, is given by:

$$\frac{\Delta L}{L}\bigg|_{Simplified} = \frac{\Delta\phi_a}{3}\frac{1+v}{1-v} \qquad (10)$$

where v is the polymer's Poisson ratio. It is also possible to show that the compressive stress experienced by the polymer due to its restrained expansion in the directions perpendicular to the optical axis (y and z in FIG. 1) is given by:

$$\sigma_\perp = \frac{\phi_a E}{3(1-v)} \qquad (11)$$

where E is the Young's modulus of the polymer. This stress will in turn lead to a volume reduction of the polymer, given by:

$$\frac{\Delta V_h}{V} = \frac{\Delta\sigma_h}{B} = \frac{2}{9}\frac{\Delta\phi_a E}{B(1-v)} \qquad (12)$$

where B is the bulk modulus of the polymer, and $\sigma_h = \frac{2}{3}\sigma\perp$ is the hydrostatic stress inside the polymer. The addition of a $\phi_a$ analyte volume fraction will lead to a $\Delta n$ variation of the polymer refractive index. Several rules may be used to predict the refractive index of binary mixtures, as known to those skilled in the art. The Lorentz-Lorenz relation is probably most frequently used. In the present analysis, the simpler Gladstone-Dale relation is chosen, which yields very similar results for the typical refractive indices that will be encountered. This relation (Eq. 13) is linear relative to $\phi_a$, leading to a simplified expression of the sensitivity ($\Gamma_\phi$).

$$\frac{\Delta n_{Mix} + \Delta n_\sigma}{n} = \Delta\phi_a\frac{(n_a - n_p)}{n_p} + \frac{\Delta V}{V}\frac{(n_p - 1)}{n_p} \qquad (13)$$

Finally, combining equations 6 and 10 to 13 into equation 7 yields the sensitivity of deformable Fabry-Perot chemical sensors in the context of the simplified analytical model:

$$\Gamma_\phi\big|_{Simplified} = \frac{\alpha}{3}\frac{1+v}{1-v} + \beta\frac{(n_a - n_p)}{n_p} + \beta\frac{2}{9}\frac{(n_p-1)}{n_p}\frac{E/B}{1-v} \qquad (14a)$$

In Eq. 14a, the first term accounts for interferometer deformations. The second term accounts for polymer refractive index variations due to mixture with an analyte of different refractive index. The third term accounts for refractive index variations due to hydrostatic stress upon expansion. The absorbent polymers used in the following experiments are essentially incompressible. For example, the bulk modulus (B=$10^3$ MPa) of Sylgard 184 PDMS is significantly higher than its Young's modulus (E=1.8 MPa), which yields a v=0.5−E/2B=0.499 Poisson's ratio. In this context, the third term of Eq. 14a is almost three (3) orders of magnitude smaller than the first two (2) terms and can be neglected. Eq. 14a can therefore be rewritten as:

$$\Gamma_\phi\big|_{Simplified} \approx \alpha + \beta\frac{(n_a - n_p)}{n_p} \qquad (14b)$$

Furthermore, for most organic compounds, the refractive index difference in Eq. 14b ($n_a-n_p$) should be in the order of 0-0.15. In these cases, it is desirable for the term that accounts for interferometer deformations (a) to be at least ten (10) times larger than the term that accounts for refractive index variations. Therefore, with $\alpha=0.75$, the absorption of, for example, $\phi_a=1\%$ of volume fraction of analyte is expected to induce a $\Delta\lambda_{res}/\lambda_{res}\approx 0.75\%$ shift of the interferometer resonance wavelength.

In order to evaluate if the response of the fabricated devices can be expected to be close to the simplified analytical case, finite element simulations were performed using CoventorWare™ 2010. An isotropic expansion of the polymer volume filling the gap between the two mirrors illustrated in FIG. 1 was simulated. Upon expansion, the relative increase of the distance between the mirrors ($\Delta L/L$) and the hydrostatic pressure inside the polymer ($\sigma_h$) were evaluated. For these simulations, the Young's modulus (E=1.8 MPa) and Poisson's ratio (v=0.499) values of Sylgard 184 PDMS were used.

Figure 4A:
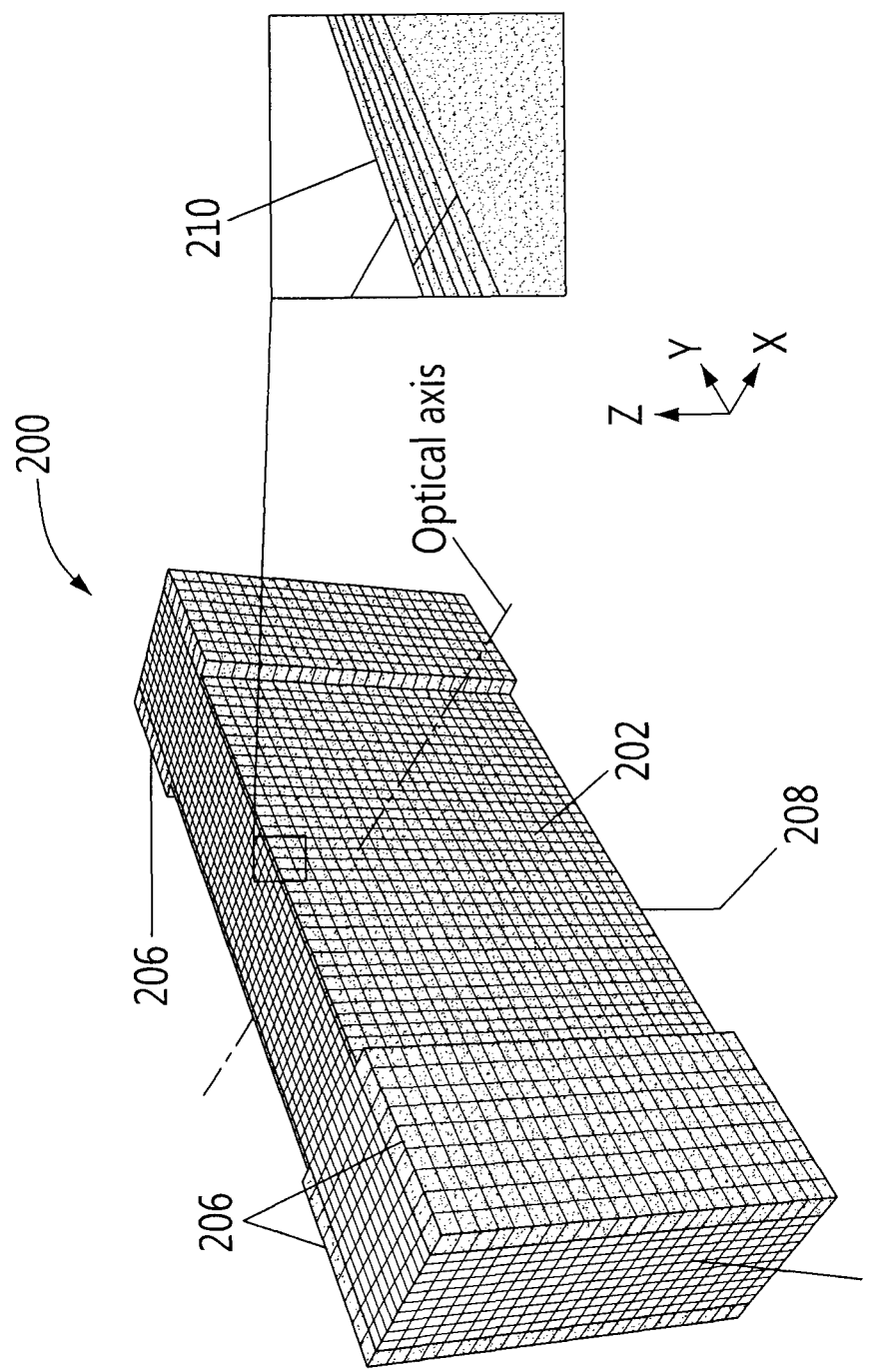
FIG. 4a is an exemplary mesh model showing boundary conditions for the simulations performed on interferometer deformation upon swelling.

The meshed model 200 used for the simulations is presented in FIG. 4a. For each of the two Bragg mirrors (references 106 in FIG. 1), only the one (flexible) silicon layer 202 that is in contact with the polymer (reference 104 in FIG. 1) is included in the model 200. The (y, z) dimensions of these layers 202 are (130 μm, 80 μm). Their thickness (in the x direction) is 600 nm, as determined by previous optical characterization of the interferometers. The layers 202 are attached at both y extremities 204 to the edges 206 of the microfluidic channel (not shown), which edges 206 are considered to be immobile. The bottom z extremities 208 of the mirror layers 202 are fixed to the substrate (not shown) while their upper z extremities (not shown) are free to move.

Two different types of boundary conditions were used to simulate the contact interfaces 210 between silicon and PDMS. The first type considers the two materials to be tightly bonded together, such that no sliding can occur. The second type considers the two materials to be in contact but to be free to slide on each other without friction. The experimental results are expected to lie somewhere between these two extreme cases, which will be referred to as the "bonded" and "sliding" models.

Only a small portion of the microfluidic channel length (40 μm) is included in the mesh model 200 on each side of the Fabry-Perot cavity. The continuation of the truncated channel must therefore be simulated using appropriate boundary conditions. It is possible to show that, away from the deformable mirror layers, no polymer movement occurs in the directions (x, y) parallel to the substrate due to the rigid boundaries of the microfluidic system. The continuation of the channels is therefore simulated using "Fix Y" boundary conditions.

For the two models, the response to various polymer volume increases was simulated. A linear relation was established between the absorbed volume fraction of analyte ($\phi_a$) and the relative pathlength increase between the mirrors (on the optical axis of the system):

$$\frac{\Delta L}{L}\bigg|_{Bonded} = 1.77\Delta\phi_a; \frac{\Delta L}{L}\bigg|_{Sliding} = 0.51\Delta\phi_a \qquad (15)$$

A linear relation was also established between $\phi_a$ and the hydrostatic stress ($\sigma_h$) inside the polymer volume where light will interact with the system (around the optical axis in FIG. 4a). As for the simplified analytical model, the hydrostatic stress ($\sigma_h$) is found to be negligible compared with the bulk modulus of PDMS based polymers. Its contribution to the sensitivity of the sensors can therefore still be neglected, as per the above.

Finally, replacing Eq. 10 by Eq. 15 yields the sensitivity of the sensors ($\Gamma_\phi$) for both the bonded and the sliding models:

$$\Gamma_\phi|_{Bonded} = 1.77\alpha + \beta\frac{(n_a - n_p)}{n_p};$$ (16)

$$\Gamma_\phi|_{Sliding} = 0.51\alpha + \beta\frac{(n_a - n_p)}{n_p}$$

Figure 4C:
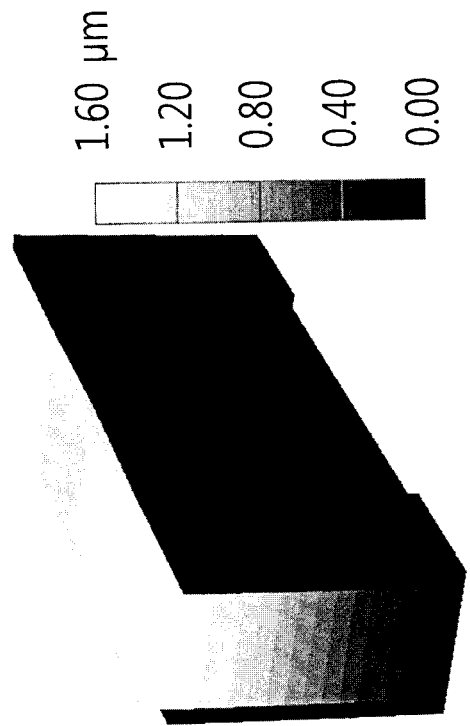
FIG. 4c is an exemplary grayscale illustration of the magnitude of deformation upon a 2% polymer volume increase for sliding silicon-PDMS material interfaces.

In Eq. 16, the sliding model yields a deformation sensitivity (0.51α) that is twice smaller than what was predicted (1.00α) by the simplified analytical model. This result was expected since the polymer is now free to expand in two directions (x, z) (see FIG. 4c) rather than only one for the analytical model (similarly, a polymer that would be free to expand in all three dimensions would yield a 0.33α sensitivity).

Figure 4B:
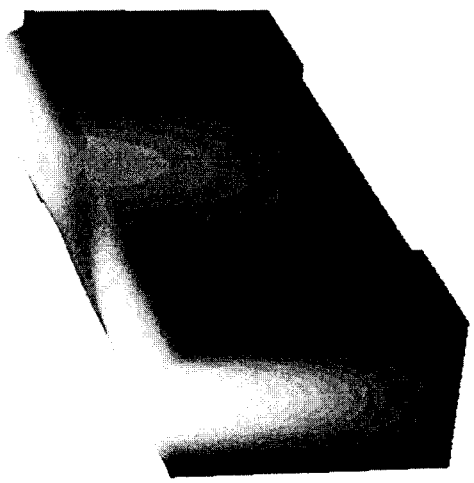
FIG. 4b is an exemplary grayscale illustration of the magnitude of deformation upon a 2% polymer volume increase for bonded silicon-phenyl-doped polydimethylsiloxane (PDMS) material interfaces.

Surprisingly, the bonded model yields a higher deformation sensitivity (1.77α) than what is predicted by the simplified analytical model in Eq. 14 (1.00α). This is because, in FIG. 4b, the polymer is not free to expand in the microchannel, on each side of the optical cavity. Consequently, the polymer located in these regions expands towards the optical axis of the system, where the deformation is amplified. However, this behavior is found to depend strongly on the polymer's Poisson ratio. For v<0.499, the predicted sensitivity of the bonded model quickly reduces and essentially matches the sensitivity of the analytical model when v<0.45.

Figure 5C:
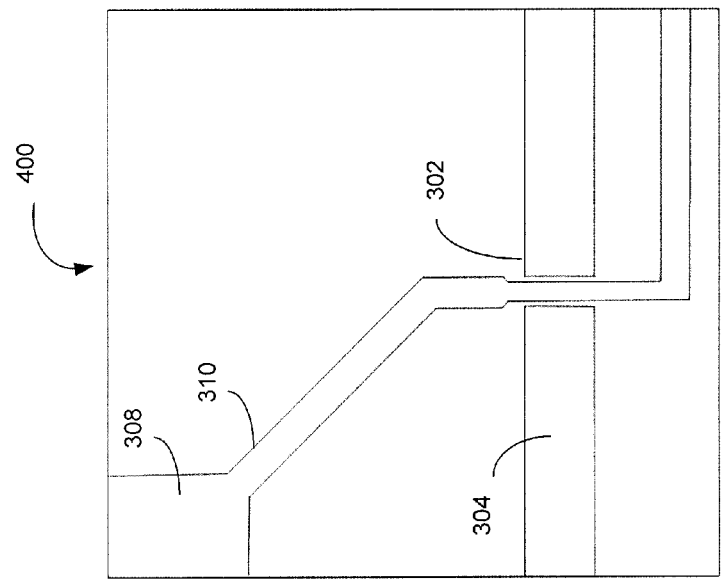
FIG. 5c is an exemplary optical micrograph of a polymer-coated device.
Figure 5A:
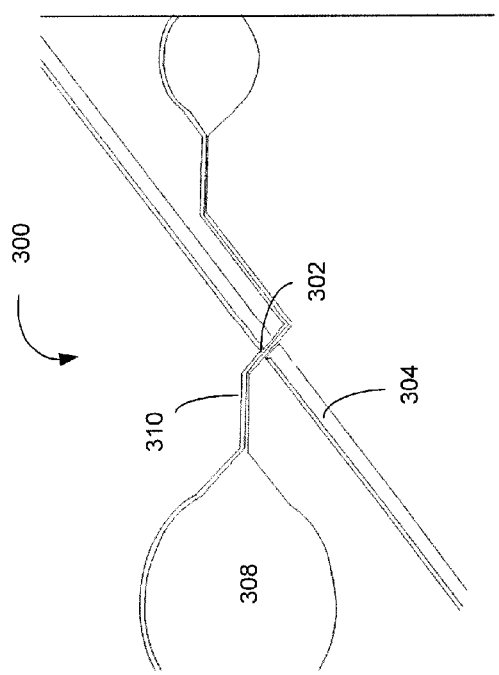
FIG. 5a illustrates an exemplary low magnification scanning electron micrograph of a sensor, prior to polymer coating, showing the monolithically integrated microfluidic system used for functionalization.
Figure 5B:
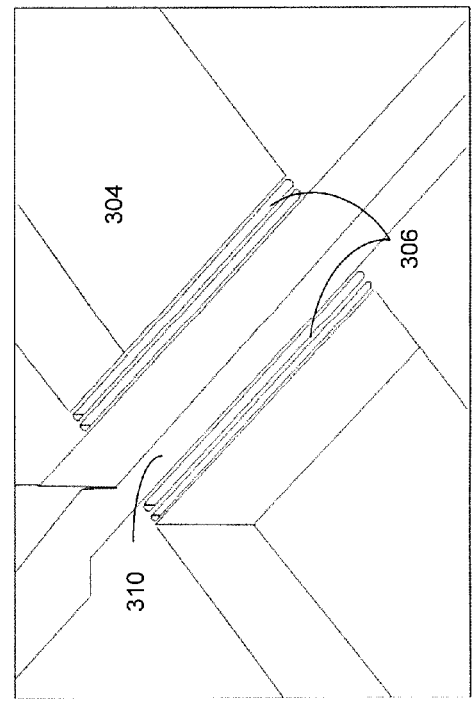

FIG. 5a illustrates a low magnification scanning electron micrograph (SEM) 300 of a sensor, prior to polymer coating, showing the monolithically integrated microfluidic system used for functionalization. FIG. 5b is a higher magnification view of the Fabry-Perot interferometer 302 and the elongate optical fiber alignment grooves 304. FIG. 5c shows an optical micrograph 400 of a polymer-coated device. The SEM as illustrated has three silicon layers per mirror. This configuration was fabricated and tested for gas detection and was found to respond similarly to deformations and refractive index changes. The interferometers as in 302 were etched in silicon wafers using an inductively coupled plasma reactor (ICP180-100, Oxford Instruments Inc.). A two-mask soft lithography process was used to fabricate successively the smaller (multilayer mirrors 306) and the larger (optical fiber alignment grooves as in 304, microfluidic system comprising a reservoir 308 and a microfluidic channel 310) features.

The absorbent polymer of FIG. 5c was inserted between the two mirrors 306 of the interferometer 302 using a monolithically integrated microfluidic system. A drop of liquid (~15-20 μL) pre-polymer mixture was placed in the reservoir 308. The polymer flowed by capillary forces in the microfluidic channel 310 to fill the gap in the interferometer 302, and was then left to cure at room temperature for several hours. Some devices required more than 12 hours of curing for stable performance, so all devices were cured for more than a week.

Two different polymers were tested for the functionalization of the interferometers. Some devices were coated with commercial PDMS (Dow Corning® Sylgard 184), while the others were functionalized with a PDMS-polydiphenylsiloxane copolymer (PDMS-PDPS). The copolymer was prepared using the following mixture proportions: 10% polydiphenylsiloxane (PDPS) mole fraction, 3% titanium tetraisopropoxide cross-linker mole fraction.

The functionalized devices were tested for the detection of two different vapor phase analytes at room temperature and atmospheric pressure. To produce different analyte concentrations, saturated vapor was first generated by bubbling nitrogen through a wash bottle containing the analyte in liquid phase. A two channels mixing flowmeter was then used to dilute back the saturated vapor with pure nitrogen, in order to lower analyte concentration. A gas cap was lowered over the sensor to allow analyte vapor to disperse evenly over the chip. The complete setup was housed inside a laminar flow hood. Cyclohexane and m-xylene were chosen as the analytes. It should be understood that any volatile compound that can partition in a polymer may also apply. Therefore, other analytes, including, but not limited to, Alcohols, Aldehydes, Ketones, Carboxyl acids, fatty acids, amines, sulfurous compounds, and aromatic compounds, i.e. benzene, toluene, ethylbenzene, and xylenes (BTEX), may apply.

Upon gas exposure, the interferometer resonance wavelength was tracked in real time by continuously scanning a tunable external-cavity diode laser source (Ando AQ4320D). The laser was interfaced with the interferometer through conventional single-mode optical fibers (Corning® SMF-28), which were cleaved and inserted in the optical fiber alignment grooves. The transmission spectrum was recorded at 30 second intervals using an InGaAs photodiode detector (Thorlabs D400FC) and a lock-in amplifier (Stanford Research Systems SRS844 RFCA). The voltage output of the lock-in amplifier was then collected using a 16-bit data acquisition USB device (Measurements Computing PMD 1608 FS) and custom-made LabView (National Instruments) software. Amplitude noise was minimized numerically in each recorded spectrum using a zero-phase shift, forward and reverse digital convolution filter (Matlab® "FILTFILT" function). A 1 nm wide Gaussian distribution (σ=0.2 nm) was used as the filter. The exact resonance wavelength position was then determined for each spectrum by fitting a fourth order polynomial to the top half of the filtered resonance peaks.

Figure 6A:
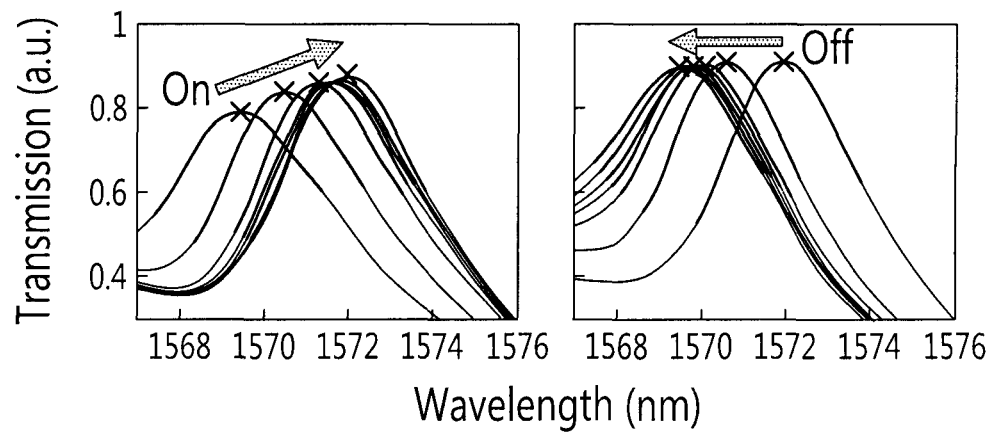
FIG. 6a is a graph illustrating measured transmission spectra of a PDMS-coated deformable FPI sensor upon exposition to a 240 ppm m-xylene vapor concentration.
Figure 6B:
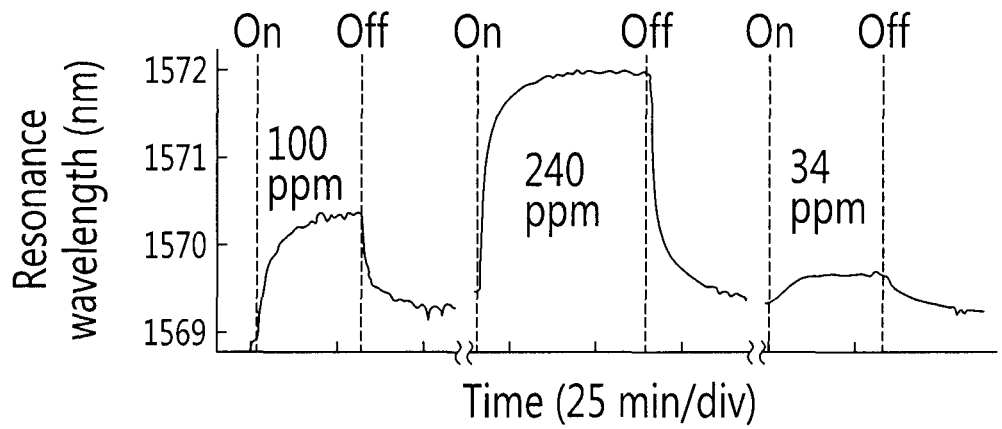
FIG. 6b is a graph illustrating the resonance wavelength of a PDMS-coated interferometer over time for concentrations of m-xylene.
Figure 6C:
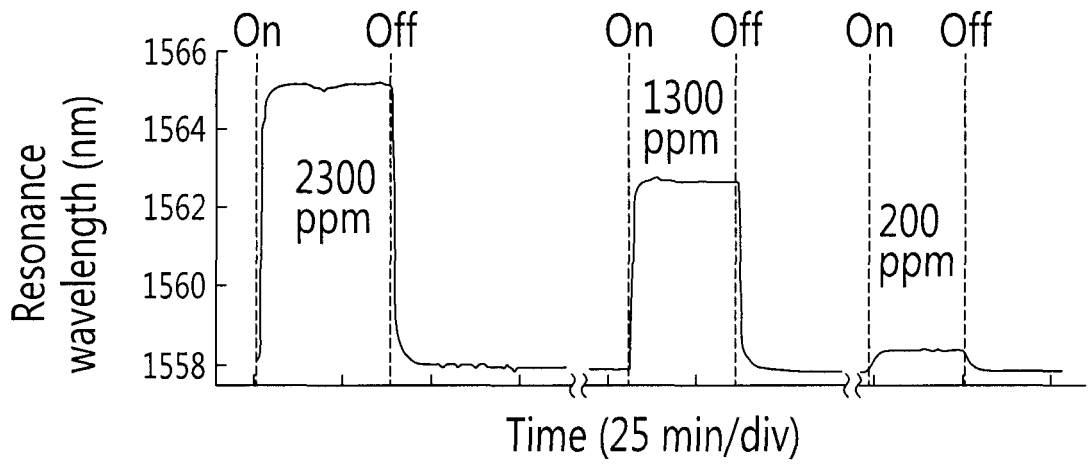
FIG. 6c is a graph illustrating the resonance wavelength of a PDMS-coated interferometer over time for concentrations of cyclohexane.

The response of the PDMS-coated interferometer to various m-xylene and cyclohexane vapor concentrations is presented in FIGS. 6a-6c. As expected, in FIG. 6a the resonance peak position is found to increase upon exposition to m-xylene, before returning to its initial value when the gas flow is switched back to pure nitrogen. In FIGS. 6b and 6c, this shift of the resonance wavelength is reported, as a function of time, for various concentrations of m-xylene (FIG. 6b) and cyclohexane (FIG. 6c). The response to 34 ppm m-xylene, the lowest concentration reachable with the flowmeter, is clearly visible. A limit of detection below this value is therefore expected.

The resonance wavelength increase ($\Delta\lambda_{Res}(t)$) follows an essentially exponential pattern (i.e.: $\Delta\lambda_{Res}(t) \propto 1-e^{-t/\tau}$) with a time constant (τ) that differs for each polymer-analyte combination. In PDMS, the response time is found to be almost four (4) times faster for cyclohexane (τ=40 sec) than for m-xylene (τ=150 sec). This faster response time however occurs at the expense of an approximately four times lower sensitivity to cyclohexane than to m-xylene.

This trade-off between sensitivity and response time is directly related to the partition coefficient ($K_{p-a}$) of each polymer-analyte combination. Higher $K_{p-a}$ values yield higher absorbed volume fractions ($\phi_a$) and therefore higher sensitivities. However, higher $K_{p-a}$ values also yield higher retention times (i.e. lower diffusion constants), which increase the time required for the analyte to diffuse completely inside the 80 μm deep polymer-filled channel.

Figure 7:
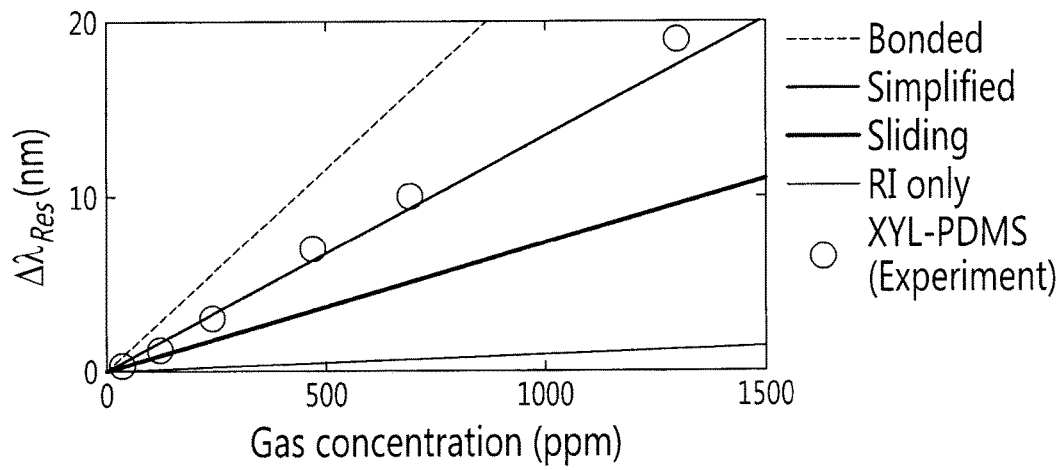
FIG. 7 is a graph illustrating experimental and simulated resonance wavelength shift as a function of m-xylene concentration.

FIG. 7 is a graphical representation of the experimental and simulated resonance wavelength shift. The resonance wavelength shift for the different m-xylene vapor exposures is compared with the analytical model (Eq. 14), and with the finite element (Eq. 16) bonded and sliding models. The expected response due only to refractive index variations is also included to highlight the influence of mechanical deformations on the sensitivity (a control experiment using undeformable mirrors was also carried out to confirm the influence of refractive index variations only). The absorbed volume fraction of analyte ($\phi_a$) is converted (Eq. 8) to v/v gas concentrations ($C_{air}$) in Eqs. 14 and 16, using a $K_{p-a}$=2090 partition coefficient for m-xylene between PDMS and air. $V_m$=0.123 L/mol was also used, as well as the refractive indices of PDMS ($n_p$=1.3959) and xylenes ($n_a$=1.4802) at λ=1550 nm.

As expected, the experimental results fall between the bonded and sliding models. The silicon-PDMS adhesion force appears to be important enough to yield a higher experimental sensitivity than the sliding model prediction. The sensitivity is, however, lower than the bonded model prediction. This could be an indication that PDMS does not bond perfectly with silicon, but is somewhat free to spatially reorganize itself upon expansion. Growing a thin layer of thermal silicon dioxide, prior to polymer coating, may be a way to increase the polymer-interferometer bonding strength and improve sensitivity. It is also possible that the bonding strength is already high enough, but that finite element bonded sensitivity was overestimated. As previously indicated, small variations of the Poisson ratio of the PDMS tend to strongly affect the bonded model sensitivity, which rapidly reaches that of the simplified analytical model.

The simplified analytical model is found to reproduce the experimental results remarkably well. A relatively good correspondence was expected since, as shown also in Eqs. 14 and 16, the simplified analytical model yields an intermediate sensitivity between the two extreme possible cases (i.e., the bonded and sliding finite element models). Therefore, for other polymers having different mechanical properties, this model could most likely provide a useful estimate of the sensitivity without repeating the time consuming finite element simulations.

Figure 8:
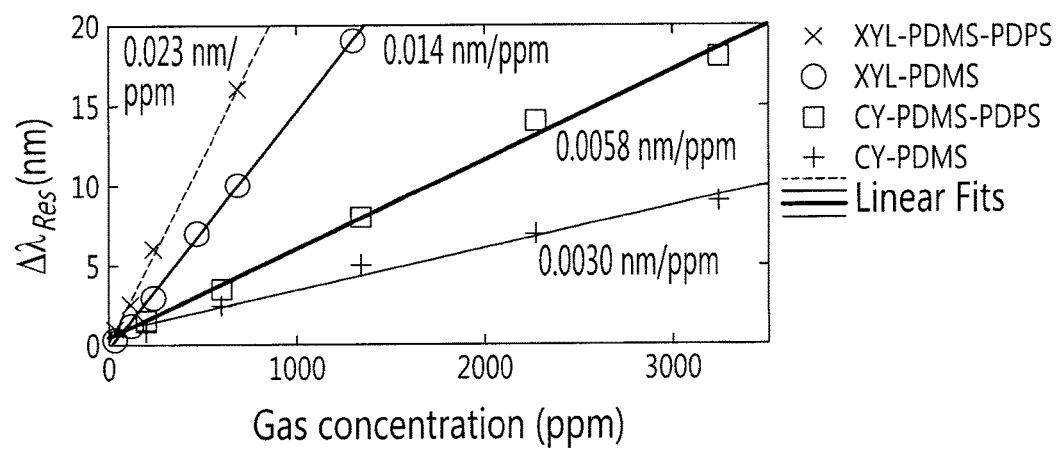
FIG. 8 is a graph illustrating an experimental response obtained for the four analyte-polymer combinations of m-xylene (XYL), cyclohexane (CY), PDMS, and the phenyl-doped copolymer (PDMS-PDPS).

In FIG. 8, there is illustrated the experimental response for m-xylene-PDMS (XYL-PDMS) and also for the three other polymer-analyte combinations. The highest sensitivity (0.023 nm/ppm) is obtained for m-xylene-PDMS-PDPS. This may be due to the addition of phenyl groups within the polymer, which could increase the polymer affinity for aromatic compounds, such as m-xylene. There are, however, other differences between the two polymers, including chain length and the type and degree of cross-linking, so other mechanical and chemical factors may also contribute to the sensitivity difference. The lowest sensitivity (0.0030 nm/ppm) is obtained for cyclohexane (CY) in PDMS, which may indicate that the partition coefficient ($K_{p-a}$) is significantly lower for cyclohexane than for m-xylene. No measurements were found in the literature for the $K_{p-a}$ of CY-PDMS, but taking the linear temperature-programmed retention index of cyclohexane (LTPRI=650) and the known relations, we expect $K_{p-a}$≅320-350. Using these values, the CY-PDMS experimental results are within the bonded and sliding models predictions.

The CY-PDMS-PDPS sensitivity (0.0058 nm/ppm) is almost two times higher than the CY-PDMS response. This was not expected initially since cyclohexane is a non-polar analyte, and since the addition of phenyl groups to PDMS tends to increase its polarity. It is possible that the phenyl groups also increase the Hildebrand solubility parameter of PDMS (initially $\delta$=7.3 cal$^{1/2}$ cm$^{-3/2}$) to a value closer to that of cyclohexane ($\delta$=8.2 cal$^{1/2}$ cm$^{-3/2}$). This phenomenon could explain a higher $K_{p-a}$ for CY-PDMS-PDPS than for CY-PDMS. However, as noted above, there are other differences between the films that may also contribute to the observed $K_{p-a}$ difference, including chain length and degree of cross-linking. Moreover, those differences may also affect the polymer mechanical properties, which could influence the sensitivity.

In FIG. 8, PDMS-PDPS showed a 64% increase in sensitivity to m-xylene and a 93% increase in sensitivity to cyclohexane as compared to PDMS. Having distinct sensitivity differences for each analyte may be useful for the development of artificial olfaction systems. For micromechanical sensors, the sensor limit of detection (LOD) is usually defined as the analyte concentration that produces a response corresponding to 3 times the standard deviation (std) of the background noise signal. In the present system, an std of 0.012 nm amplitude noise was calculated from the traces of FIGS. 6b and 6c, and also from the trace of a PDMS-PDPS coated device. Using the sensitivities of FIG. 8, it is expected that a LOD of 1.6 ppm m-xylene and 6.3 ppm cyclohexane be reached.

The structure illustrated is provided for efficiency of teaching the present embodiment. The embodiments of the invention described above are intended to be exemplary only. The scope of the invention is therefore intended to be limited solely by the scope of the appended claims.

The invention claimed is:

1. A deformable interferometric sensor comprising:
a pair of parallel and spaced apart reflectors forming a Fabry-Perot cavity, each one of the reflectors having an outer surface and an inner surface, the pair of reflectors separated by a distance L;
an optical fiber interfaced with the outer surface of each one of the reflectors and having an optical axis that intersects the pair of reflectors; and
a polymer provided between the reflectors, the polymer exhibiting expansion along the optical axis of the optical fiber upon absorption of at least one analyte, and inducing a shift of a resonance wavelength substantially proportional to a concentration of the at least one analyte as absorbed, the expansion causing an increase in the distance L between the reflectors and deforming the Fabry-Perot cavity, wherein the polymer has opposite sides and is provided between the reflectors with each one of the opposite sides adjacent a corresponding one of the reflectors, and the expansion of the polymer is constrained by the corresponding one of the reflectors.

2. The sensor of claim 1, wherein at least one of the reflectors is fixed and has a spring constant $K_{reflector}$ and the polymer has a spring constant $K_{poly}$ greater than the spring constant $K_{reflector}$ such that the expansion of the polymer causes a deformation of the at least one of the reflectors, thereby increasing the distance L between the reflectors and deforming the Fabry-Perot cavity.

3. The sensor of claim 2, wherein the spring constant $K_{poly}$ is given by:

$$K_{poly} = \frac{whE_{poly}}{L},$$

and the spring constant $K_{reflector}$ as follows:

$$K_{reflector} < \frac{whE_{poly}}{L},$$

where $E_{poly}$ is a Young's modulus of the polymer, w a width of each one of the reflectors, and the a height of each one of the reflectors.

4. The sensor of claim 3, wherein a condition for the deformation of the at least one of the reflectors is given by:

$$\frac{t^3}{w^4} < \frac{E_{Poly}}{32E_{Si}L},$$

where the at least one of the reflectors comprises a silicon layer having a Young's modulus $E_{si}$ and each one of the reflectors has a thickness t.

5. The sensor of claim 1, wherein at least one of the reflectors is displaceable by means of a displacement mechanism connected thereto, the displacement mechanism comprising a biasing member having a spring constant $K_{bias}$ lower than a spring constant $K_{poly}$ of the polymer such that the expansion of the polymer causes a change in deflection of the biasing member and the displacement of the at least one of the reflectors, thereby increasing the distance L between the reflectors and deforming the Fabry-Perot cavity.

6. The sensor of claim 1, wherein at least one of:
the deformation of the Fabry-Perot cavity and the increase in the distance L between the reflectors,
a first variation in a refractive index of the polymer resulting from mixture of the polymer with the at least one analyte upon the absorption thereof, the at least one analyte having a refractive index different than the refractive index of the polymer, and
a second variation in the refractive index of the polymer resulting from a hydrostatic stress experienced by the polymer upon the expansion thereof, the hydrostatic stress created by the reflectors opposing at least one force to the expansion
causes the polymer to induce the shift of the resonance wavelength.

7. The sensor of claim 1, wherein the reflectors are Bragg mirrors each comprising at least two layers of silicon formed in a substrate of optical material by vertical plasma etching.

8. The sensor of claim 1, wherein the reflectors comprise a reflective metallic layer, a multilayer assembly of materials exhibiting refractive index contrast, or a combination thereof.

9. The sensor of claim 1, wherein the optical fiber is one of a single mode fiber and a multi-mode fiber.

10. The sensor of claim 1, further comprising a first and a second elongated groove configured to respectively receive therein a first one and a second one of the optical fiber and to align the first and second ones of the optical fiber.

11. A method for determining a concentration of an analyte, the method comprising:
providing a polymer inside a Fabry-Perot cavity formed by a pair of parallel and spaced apart reflectors, wherein the polymer has opposite sides and is provided between the reflectors with each one of the opposite sides adjacent a corresponding one of the reflectors, the polymer exhibiting expansion and causing deformation of the cavity upon absorption of the analyte, the polymer having a spring constant $K_{poly}$ greater than a spring constant of at least one of the reflectors $K_{reflector}$;
measuring a shift of a resonance wavelength induced by expansion of the polymer; and
converting the shift of the resonance wavelength into the concentration of the analyte.

12. The method of claim 11, wherein providing the polymer inside the Fabry-Perot cavity comprises providing a microfluidic channel in a space between the reflectors, providing a reservoir in fluid communication with the microfluidic channel, placing the polymer in the reservoir, the polymer flowing by a capillary force from the reservoir into the microfluidic channel to fill the space between the reflectors, and curing the polymer at room temperature for a predetermined time period.

13. The method of claim 11, wherein providing the polymer comprises providing the polymer where the spring constant $K_{poly}$ is given by:

$$K_{poly} = \frac{whE_{poly}}{L},$$

and the spring constant $K_{reflector}$ as follows:

$$K_{reflector} < \frac{whE_{poly}}{L},$$

where $E_{poly}$ is a Young's modulus of the polymer, w a width of each one of the reflectors, h a height of each one of the reflectors, and L is a distance between the reflectors.

14. The method of claim 13, wherein providing the polymer comprises providing the polymer where a condition for a deformation of at least one of the reflectors caused by the expansion of the polymer is given by:

$$\frac{t^3}{w^4} < \frac{E_{Poly}}{32E_{Si}L},$$

where the at least one of the reflectors comprises a silicon layer having a Young's modulus $E_{si}$, and each one of the reflectors has a thickness t.

15. The method of claim 11, wherein measuring the shift of the resonance wavelength induced by expansion of the polymer comprises:
scanning a tunable laser source interfaced with the Fabry-Perot cavity through an optical fiber, the optical fiber interfaced with an outer surface of each one of the reflectors;
recording using a photodetector at least one transmission spectrum of the Fabry-Perot cavity at predetermined time intervals;
determining a position of the resonance wavelength of the recorded at least one transmission spectrum; and comparing the determined position of the resonance wavelength to an initial position of the resonance wavelength for obtaining the shift.

16. The method of claim 15, further comprising applying a filter to the recorded at least one transmission spectrum, thereby obtaining a plurality of filtered resonance peaks, and wherein determining the position of the resonance wavelength comprises fitting a fourth order polynomial to a top half of the filtered resonance peaks.

* * * * *